(12) United States Patent
Ghannoum et al.

(10) Patent No.: US 8,414,546 B2
(45) Date of Patent: Apr. 9, 2013

(54) TIP ASSEMBLY

(75) Inventors: Ziad R. Ghannoum, Trabuco Canyon, CA (US); Sean C. Madden, Mission Viejo, CA (US); Glenn Sussman, Laguna Niguel, CA (US); John R. Underwood, Laguna Niguel, CA (US)

(73) Assignee: Novartis AG, Basel (CH)

( * ) Notice: Subject to any disclaimer, the term of this patent is extended or adjusted under 35 U.S.C. 154(b) by 1586 days.

(21) Appl. No.: 10/641,947

(22) Filed: Aug. 15, 2003

(65) Prior Publication Data
US 2005/0038417 A1 Feb. 17, 2005

(51) Int. Cl.
*A61M 52/00* (2006.01)
(52) U.S. Cl.
USPC ............................................. 604/264; 604/21
(58) Field of Classification Search .................. 604/264, 604/22, 27, 107, 21, 272–274, 96.01, 164.01, 604/523, 181, 187; 128/305
See application file for complete search history.

(56) References Cited

U.S. PATENT DOCUMENTS

| 3,818,913 | A | | 6/1974 | Wallach |
| 3,930,505 | A | | 1/1976 | Wallach |
| 4,674,502 | A | * | 6/1987 | Imonti ........................ 606/177 |
| 5,562,692 | A | | 10/1996 | Bair |
| 5,616,120 | A | | 4/1997 | Andrew et al. |
| 5,669,923 | A | * | 9/1997 | Gordon ........................ 606/170 |
| 5,674,226 | A | | 10/1997 | Doherty et al. |
| 5,735,815 | A | | 4/1998 | Bair |
| 5,853,384 | A | | 12/1998 | Bair |
| 5,865,790 | A | | 2/1999 | Bair |
| 5,885,243 | A | | 3/1999 | Capetan et al. |
| 6,110,162 | A | | 8/2000 | Sussman et al. |
| 6,179,805 | B1 | | 1/2001 | Sussman et al. |
| 6,440,103 | B1 | | 8/2002 | Hood et al. |
| 6,527,766 | B1 | | 3/2003 | Bair |

* cited by examiner

*Primary Examiner* — Kevin C Sirmons
*Assistant Examiner* — Phillip Gray
(74) *Attorney, Agent, or Firm* — Kenneth Bassinger

(57) ABSTRACT

A tip assembly for a liquefaction surgical handpiece. The tip assembly has an inner connector and an outer cap. The outer cap contains an external thread for attaching the tip assembly to a handpiece. The inner housing contains an alignment tab and fits within the outer cap so as to allow rotation of the inner connector within the outer cap. The inner and outer liquefaction tip tubes are frictionally fit into a bore in the inner connector. The proximal end of the inner housing contains a gasket that seal the inner housing against the handpiece.

4 Claims, 1 Drawing Sheet

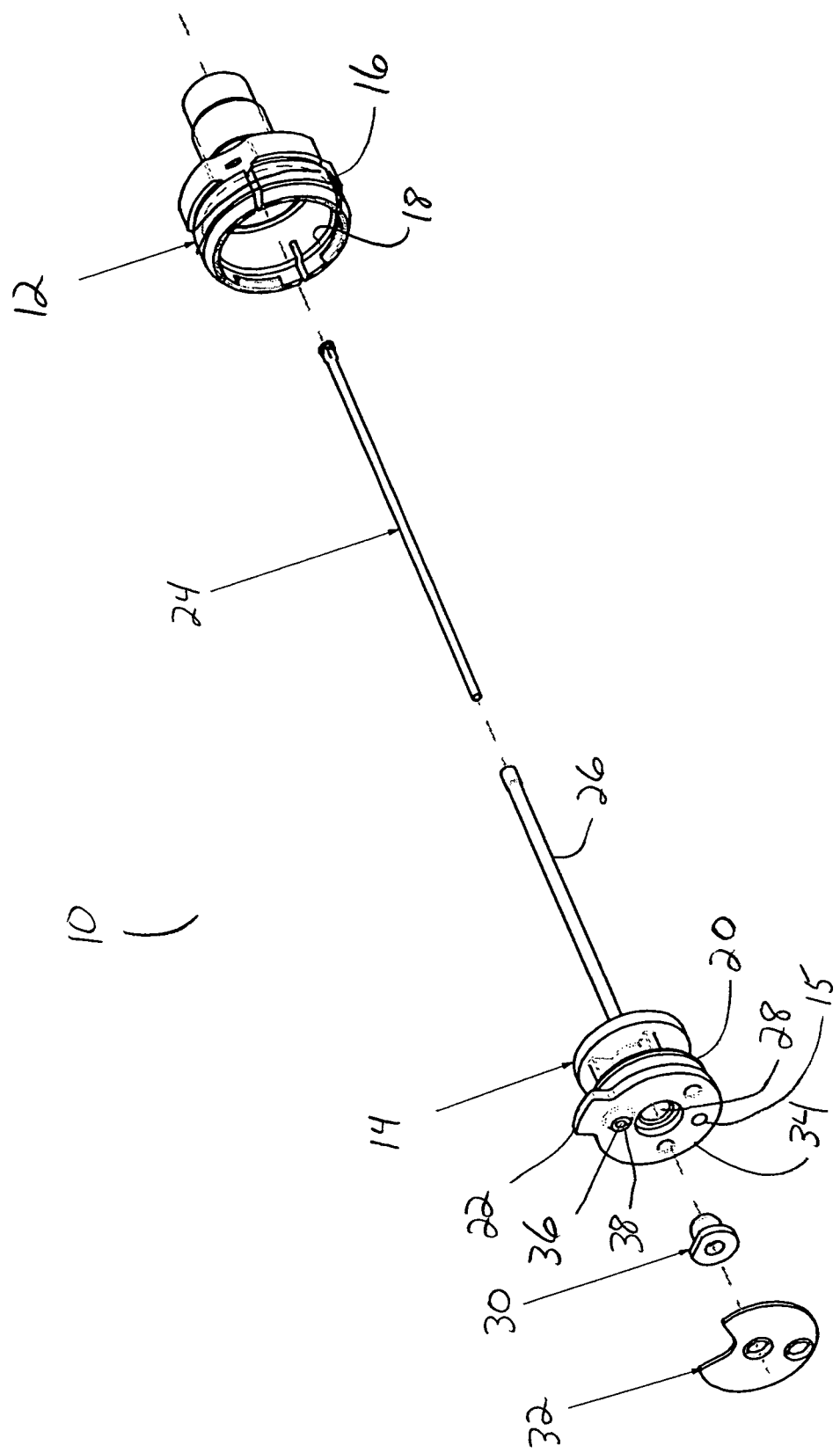

TIP ASSEMBLY

BACKGROUND OF THE INVENTION

This invention relates generally to the field of cataract surgery and more particularly to a tip assembly for use on a liquefaction handpiece.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted with the injection of the heated solution and the introduction of a relatively cool irrigating solution, thereby quickly cooling and removing the heated solution. This technique is more fully described in U.S. Pat. No. 5,616,120 (Andrew, et al.), the entire contents of which is incorporated herein by reference.

Handpiece and tips suitable for practicing this technique are described in U.S. Pat. Nos. 5,989,212, 5,997,499, 6,080,128, 6,110,162, 6,179,805 and 6,206,848 (Sussman, et al.), the entire contents of which being incorporated herein by reference. These patents do not disclose any details on how to connect the tip to the handpiece.

Therefore, a need continues to exist for an assembly for connecting a tip to a handpiece.

BRIEF SUMMARY OF THE INVENTION

The present invention improves upon the prior art by providing a tip assembly for a liquefaction surgical handpiece. The tip assembly has an inner connector and an outer cap. The outer cap contains an external thread for attaching the assembly to a handpiece. The inner connector contains an alignment tab and fits within the outer cap so as to allow rotation of the inner connector within the outer cap. The inner and outer liquefaction tip tubes are frictionally fit into a bore in the inner connector. The proximal end of the inner connector contains a gasket that seal the inner connector against the handpiece.

Accordingly, one objective of the present invention is to provide a tip connector for a liquefaction surgical handpiece.

Another objective of the present invention is to provide a tip connector having an inner housing that rotates within an outer cap.

Another objective of the present invention is to provide a tip connector having an inner housing with an alignment tab.

These and other advantages and objectives of the present invention will become apparent from the detailed description and claims that follow.

BRIEF DESCRIPTION OF THE DRAWINGS

The FIGURE is an exploded perspective view of a tip using the connector of the present invention.

DETAILED DESCRIPTION OF THE INVENTION

Tip assembly 10 of the present invention generally includes outer cap 12 and inner connector 14. Cap 12 is generally hollow and contains external thread 16 and internal groove 18. Thread 16 allows cap 12 to be screw-fitted to a handpiece (not shown) so as to hold assembly 10 to the handpiece. Inner connector 14 contains annular ridge 20 that snap fits within groove 18, thereby hold connector 14 within cap 12, but allowing connector 14 to rotate within cap 12. Connector 14 also contains alignment tab 22 that fits within a corresponding slot in the handpiece (not shown), thereby aligning assembly 10 with the handpiece. Connector 14 may contain a first bore 15 that permits cooled or ambient irrigation fluid to pass through connector 14. Cap 12 and connector 14 are preferably molded from a suitable thermoplastic.

Assembly 10 further contains inner injection tube 24 that telescopically fits within outer injection tube 26. Inner tube 24 and outer tube 26 are received in second bore 28 in connector 14. Outer tube 26 is retained and sealed in connector 14 by ring plug 30. Inner tube 24 passes through and seals against plug 30. Third bore 36 in connector 14 fluidly communicates with second bore 28 and the interior of outer tube 26. Raised boss 38 surrounds third bore 36 and helps to insure a pressure tight seal by, for example, fitting within a mating countersink in the handpiece (not shown). Gasket 32 is applied to proximal end 34 of connector 14 by adhesive or other suitable method. Gasket 32 preferably is silicone rubber and seals assembly 10 to the handpiece.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating cutting tips to enhance performance.

We claim:

1. A tip assembly, comprising:
   a) a generally hollow outer cap;
   b) an inner connector that is received and retained in the outer cap so as to allow rotational movement of the inner connector within the outer cap, the inner connector having an alignment tab, a generally planar exterior surface, a first bore, and a second bore, the first bore in fluid communication with the second bore, the first and second bores both terminating on the generally planar exterior surface of a proximal end of the inner connector;
   c) an outer tube received in the first bore in the inner connector and sealed within the inner connector by a plug located at the proximal end of the outer tube, the outer tube terminating at the connector, an interior of the outer tube in fluid communication with the second bore; and
   d) an inner tube telescopically received in the outer tube, the inner tube sealed against the plug.

2. The tip assembly of claim 1 wherein the inner connector further comprises a sealing boss around the second bore.

3. The tip assembly of claim 1 wherein the inner tube passes through the plug.

4. The tip assembly of claim 1 further comprising a gasket on the proximal end of the inner connector.

* * * * *